United States Patent
Ramadan et al.

(10) Patent No.: US 8,652,176 B2
(45) Date of Patent: Feb. 18, 2014

(54) POLYAXIAL SCREW CONNECTION ASSEMBLY

(75) Inventors: Mohamed Ahmed Hafez Ramadan, Cairo (EG); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 853 days.

(21) Appl. No.: 12/474,925

(22) Filed: May 29, 2009

(65) Prior Publication Data
US 2010/0305614 A1    Dec. 2, 2010

(51) Int. Cl.
*A61B 17/70*    (2006.01)
(52) U.S. Cl.
USPC .................... 606/264; 606/246; 606/250
(58) Field of Classification Search
USPC ............. 606/246–279; 403/53, 56, 62, 90
See application file for complete search history.

(56) References Cited

U.S. PATENT DOCUMENTS

| | | | | |
|---|---|---|---|---|
| 7,163,539 | B2 * | 1/2007 | Abdelgany et al. | 606/86 A |
| 2004/0116928 | A1 * | 6/2004 | Young et al. | 606/61 |
| 2005/0187548 | A1 * | 8/2005 | Butler et al. | 606/61 |
| 2007/0173829 | A1 * | 7/2007 | Drewry et al. | 606/61 |

* cited by examiner

*Primary Examiner* — Jerry Cumberledge
*Assistant Examiner* — Nicholas Plionis
(74) *Attorney, Agent, or Firm* — Rahman LLC

(57) ABSTRACT

A polyaxial screw connection assembly includes a first longitudinal member comprising a bored fastener channel and a first bulbous body; a second longitudinal member comprising a cylindrical body to fit within the fastener channel, and a second bulbous body; a fastener with a bored cylindrical channel, connected to the first longitudinal member and the cylindrical body and securely couples the first longitudinal member to the second longitudinal member; a first fixation component directly connected to the first bulbous body; a second fixation component directly connected to the second bulbous body; a first pin engaged within the first longitudinal member via a bored first channel and contacting the first bulbous body causing the first bulbous body to outwardly expand; and a second pin engaged within the second longitudinal member via a bored second channel and contacting the second bulbous body causing the second bulbous body to outwardly expand.

12 Claims, 24 Drawing Sheets

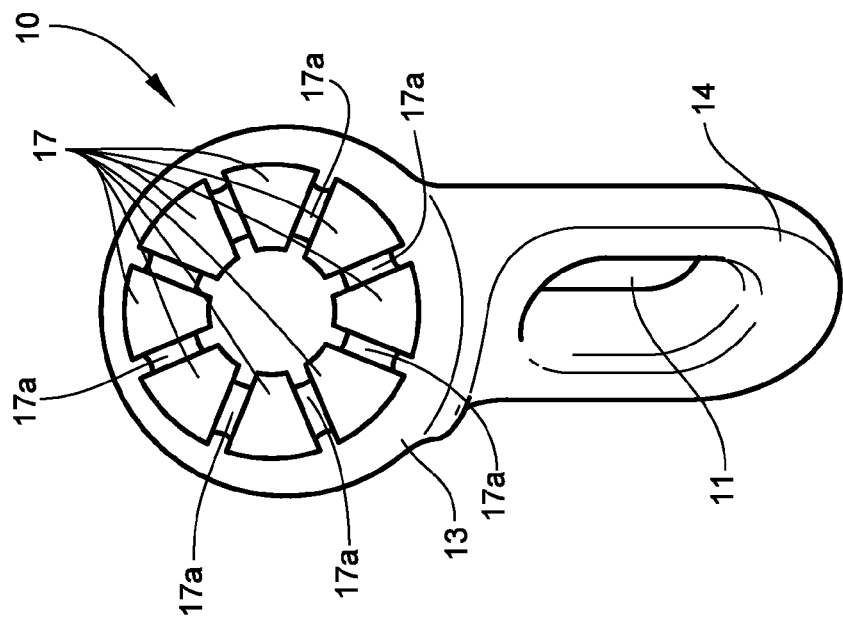
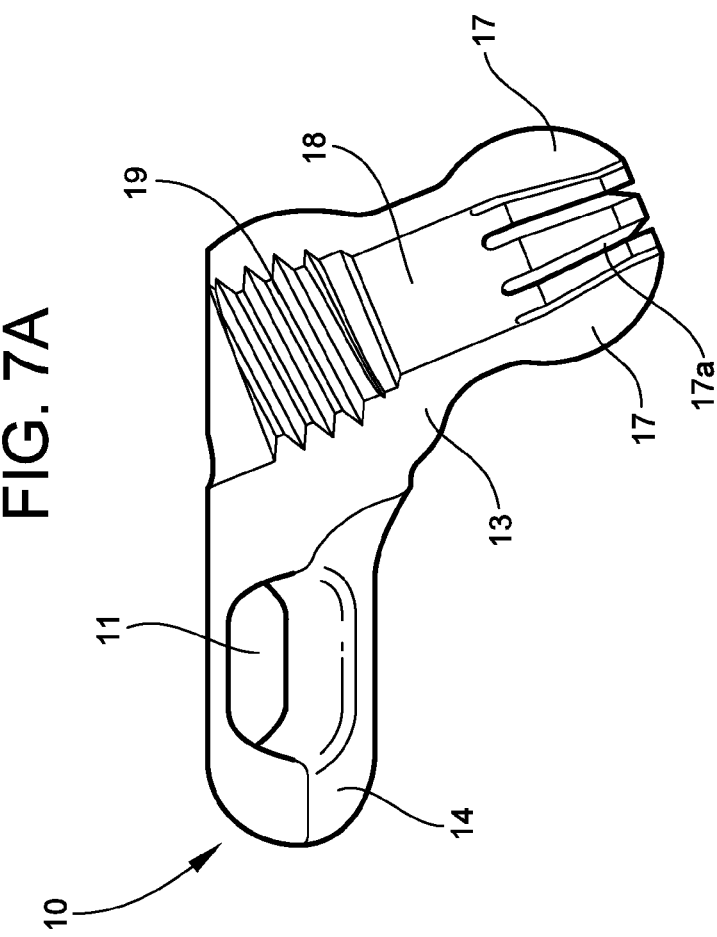
FIG. 7B
FIG. 7A

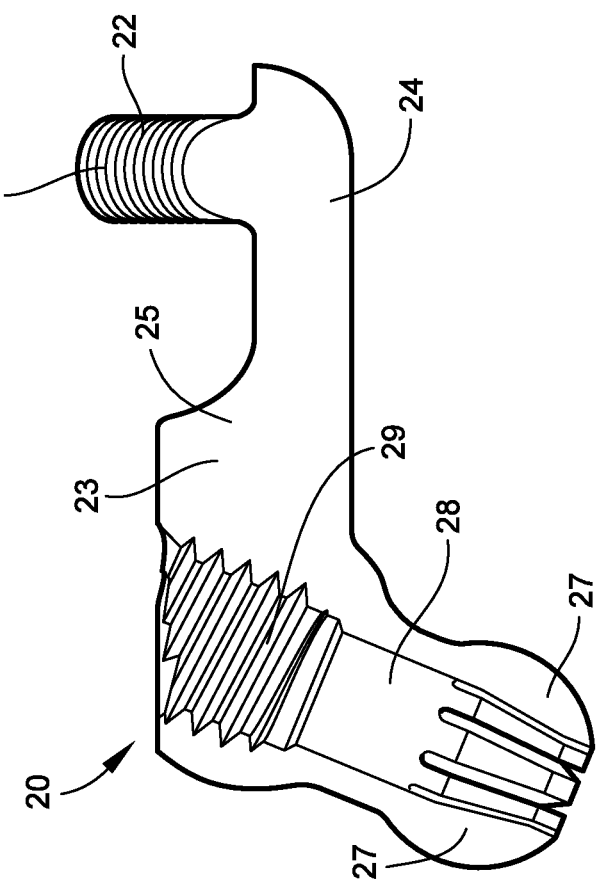
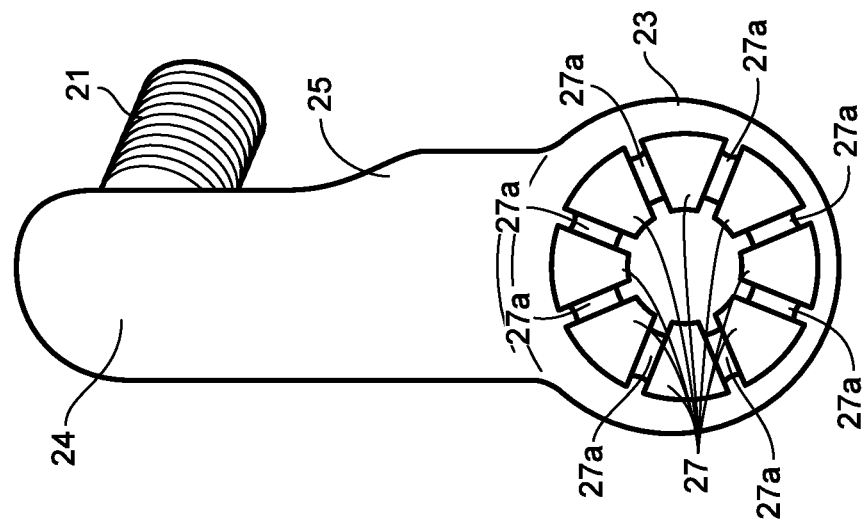
FIG. 15(A)
FIG. 15(B)

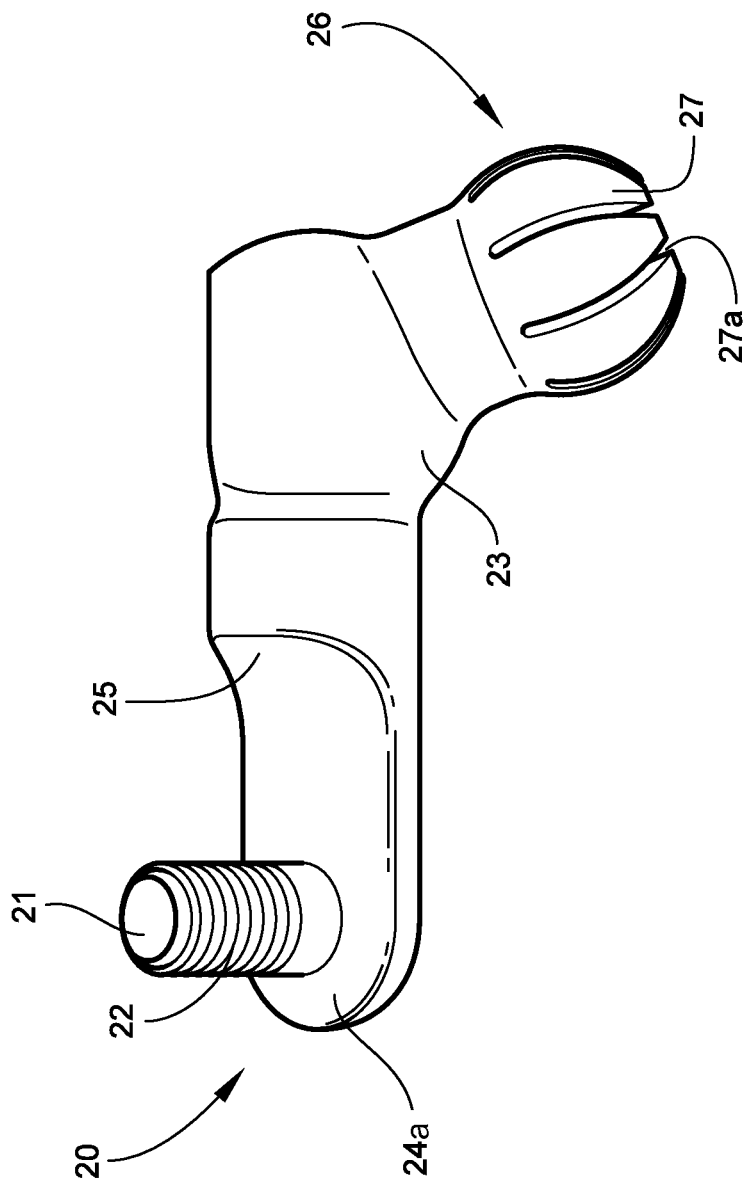

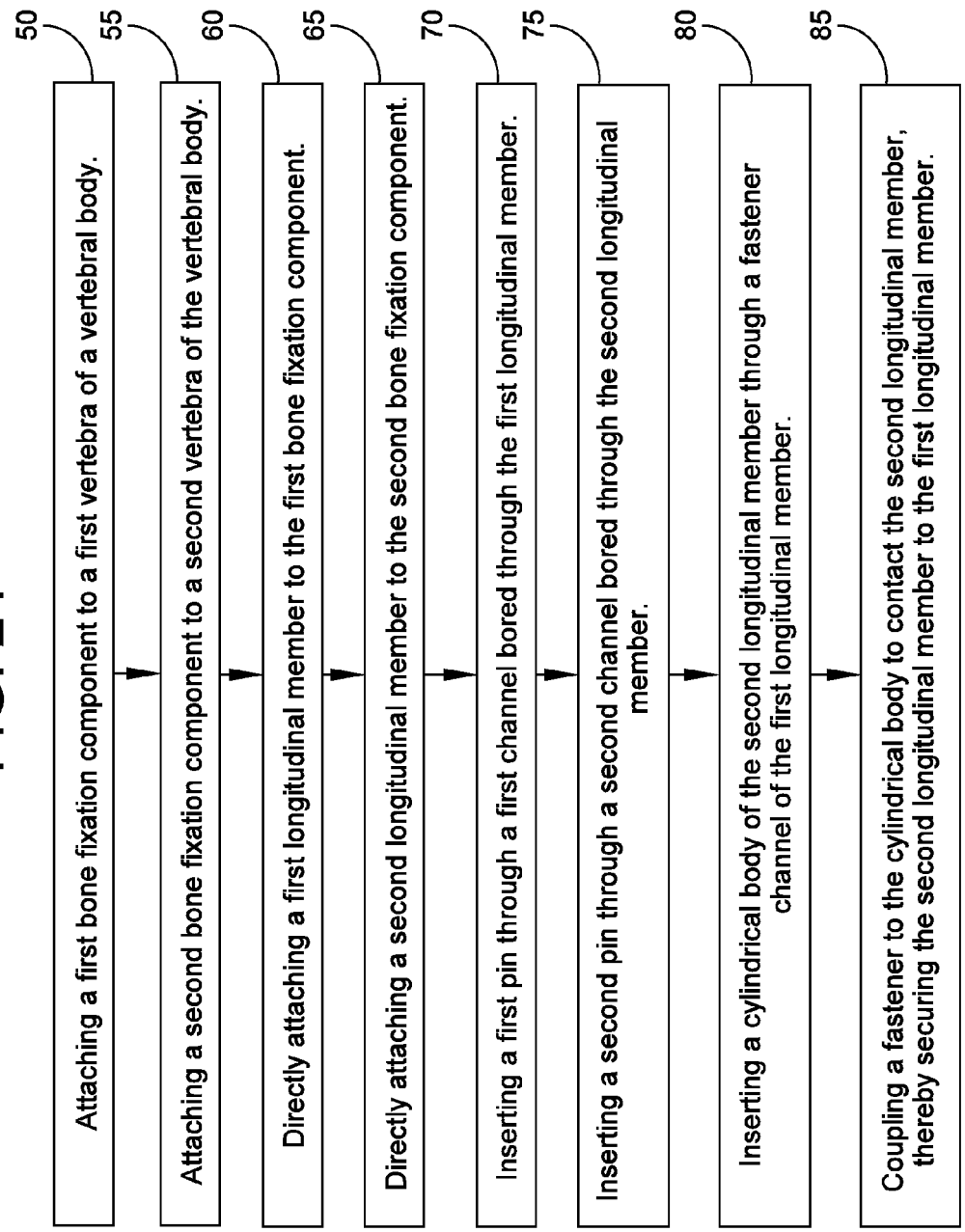

POLYAXIAL SCREW CONNECTION ASSEMBLY

BACKGROUND

1. Technical Field

The embodiments herein generally relate to medical devices and assemblies, and more particularly to coupling orthopedic surgical implant assemblies together.

2. Description of the Related Art

Surgical procedures treating spinal injuries are one of the most complex and challenging surgeries for both the patient and the surgeon. When there are various deformities, trauma, or fractures of the vertebra, surgeons may attempt to "fuse" them together by attaching screw-like devices into the pedicles of the spine and thereby connecting several vertebrae (typically two or more) using a semi-rigid rod. However, due to the complexity of the human anatomy, most surgeons must bend the rod (causing notches thereby reducing fatigue resistance) before placing them into two or more non-aligned pedicle screws in order to properly stabilize the pedicle screw assembly within the patient's body.

Depending on the purpose of the spine surgery, indications, and patient size, surgeons must pre-operatively choose between different spinal systems with differing rod sizes pre-operatively sometimes causing delays in surgery while waiting for more adequate systems to be sterilized. Some surgeons prefer monoaxial screws for rigidity, while some sacrifice rigidity for surgical flexibility in screw placement. Therefore, a system is needed to accommodate both theories. For example, during scoliosis surgery conventional polyaxial systems typically cannot lock into a desired position to persuade the spinal column into desired correction before final construct assembly.

Most conventional top loading polyaxial spine screws do not do enough to address cantilever failure of the assembly components. Additionally, conventional systems require several different components to be manipulated and assembled by the surgeon during a surgical procedure. Reducing the number of components in a screw assembly that are manipulated and assembled would simplify operating room logistics; the steps performed by the surgeon during the surgical procedure; and, ultimately, improve patient recovery time.

SUMMARY

In view of the foregoing, an embodiment herein provides an assembly comprising a first longitudinal member comprising a fastener channel bored therethrough and an outwardly protruding and expandable round first bulbous body; a second longitudinal member comprising an outwardly protruding cylindrical body, dimensioned to fit within the fastener channel, and an outwardly protruding and expandable round second bulbous body; a fastener with a cylindrical channel bored therethrough, connected to the first longitudinal member and the cylindrical body of the second longitudinal member and securely couples the first longitudinal member to the second longitudinal member; a first fixation component directly connected to the first bulbous body wherein the first fixation component receives the first bulbous body; a second fixation component directly connected to the second bulbous body wherein the second fixation component receives the second bulbous body; a first pin engaged within the first longitudinal member via a first channel bored therethrough and contacting the first bulbous body causing the first bulbous body to outwardly expand; and a second pin engaged within the second longitudinal member via a second channel bored therethrough and contacting the second bulbous body causing the second bulbous body to outwardly expand.

The assembly may also provide the first fixation component comprising a first concave socket that receives the first bulbous body of the first longitudinal member and the second fixation component comprises a second concave socket that receives the second bulbous body of the second longitudinal member. Moreover, the assembly may provide wherein at least one of the first channel and second channel comprises threads.

The assembly may also provide the fastener that includes threads etched on an inner perimeter of the cylindrical channel. The fastener may also include a slit along a longitudinal axis thereof. In addition, the fastener may be substantially polygonal in shape. The fastener may further include a ridge along an outer perimeter of the fastener and dimensioned to engage the concentric grooves etched into the top surface of the first longitudinal member Furthermore, the assembly may provide the first longitudinal member that includes concentric grooves etched into a top surface of the first longitudinal member. The assembly may also provide at least one of the first longitudinal member and the second longitudinal member includes a lower body coupled to a main body by a sloping wall. Moreover, the sloping wall may be a 45-degree incline. In addition, the lower body may be offset along a longitudinal axis of the main body by 45-degrees.

An assembly is also provided that comprises a longitudinal member comprising a fastener channel bored therethrough and an outwardly protruding and expandable round bulbous body; a fixation component directly connected to the bulbous body, wherein the fixation component receives the bulbous body; and a pin engaged within the longitudinal member via a first channel bored through the longitudinal member and contacting the bulbous body causing the bulbous body to outwardly expand.

Such an assembly may further provide the longitudinal member to include a lower body coupled to a main body by a sloping wall. In addition, the fastener channel may be bored through the lower portion. Moreover, the sloping wall may be a 45-degree incline. Furthermore, a shape of the fastener channel may be elliptical.

An assembly is further provide that comprises a pair of longitudinal members each comprising a fastener channel bored therethrough and an outwardly protruding and expandable round bulbous body; a pair of fixation components, wherein each fixation component is directly connected to the bulbous body, wherein each the fixation component receives a corresponding the bulbous body; a pair of pins, wherein each pin is engaged within each the longitudinal member via the first channel and contacts each the bulbous body causing the bulbous body to outwardly expand; and exactly one fastener comprising a cylindrical channel bored therethrough, connecting the pair of longitudinal members to each other.

Such an assembly further provides each longitudinal member includes a lower body coupled to a main body by a sloping wall. In addition, the sloping wall may be a 45-degree incline. Moreover, at least one of the longitudinal members comprises a plurality of grooves etched therein. Furthermore, the plurality of grooves may be spaced apart from one another.

A method of engaging a pedicle fixation assembly to a vertebral body is also provided, the method comprising attaching a first bone fixation component to a first vertebra of the vertebral body, wherein the first bone fixation component comprises a first open concave socket; attaching a second bone fixation component to a second vertebra of the vertebral body, wherein the second bone fixation component comprises a second open concave socket; directly attaching a first longitudinal member to the first bone fixation component, wherein the first longitudinal member comprises a fastener channel and an outwardly protruding and expandable round first bulbous body that fits into the first concave socket; directly attaching a second longitudinal member to the second bone fixation component, wherein the second longitudinal member comprises an outwardly protruding cylindrical body dimensioned to fit within the fastener channel and an outwardly protruding and expandable round second bulbous body that fits into the second concave socket; inserting a first pin through a first channel bored through the first longitudinal member to contact the first bulbous body causing the first bulbous body to outwardly expand into the first concave socket; inserting a second pin through a second channel bored through the second longitudinal member to contact the second bulbous body causing the second bulbous body to outwardly expand into the second concave socket; inserting the cylindrical body of the second longitudinal member through the fastener channel of the first longitudinal member; and coupling a fastener to the cylindrical body to contact the first longitudinal member, thereby securing the second longitudinal member to the first longitudinal member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 7(A) illustrates a cross-sectional view of a first longitudinal member, according to an embodiment described herein;

FIG. 7(B) illustrates a bottom view of the bulbous end of a first longitudinal member, according to an embodiment described herein;

FIG. 15(A) illustrates a cross-sectional view of a second longitudinal member, according to an embodiment described herein;

FIG. 15(B) illustrates a bottom view of the bulbous end of a second longitudinal member, according to an embodiment described herein;

FIG. 16 is a front perspective view of a second longitudinal member, according to an embodiment described herein;

FIG. 24 is a flow diagram illustrating a preferred method according to an embodiment herein.

DETAILED DESCRIPTION OF PREFERRED EMBODIMENTS

Figure 1:
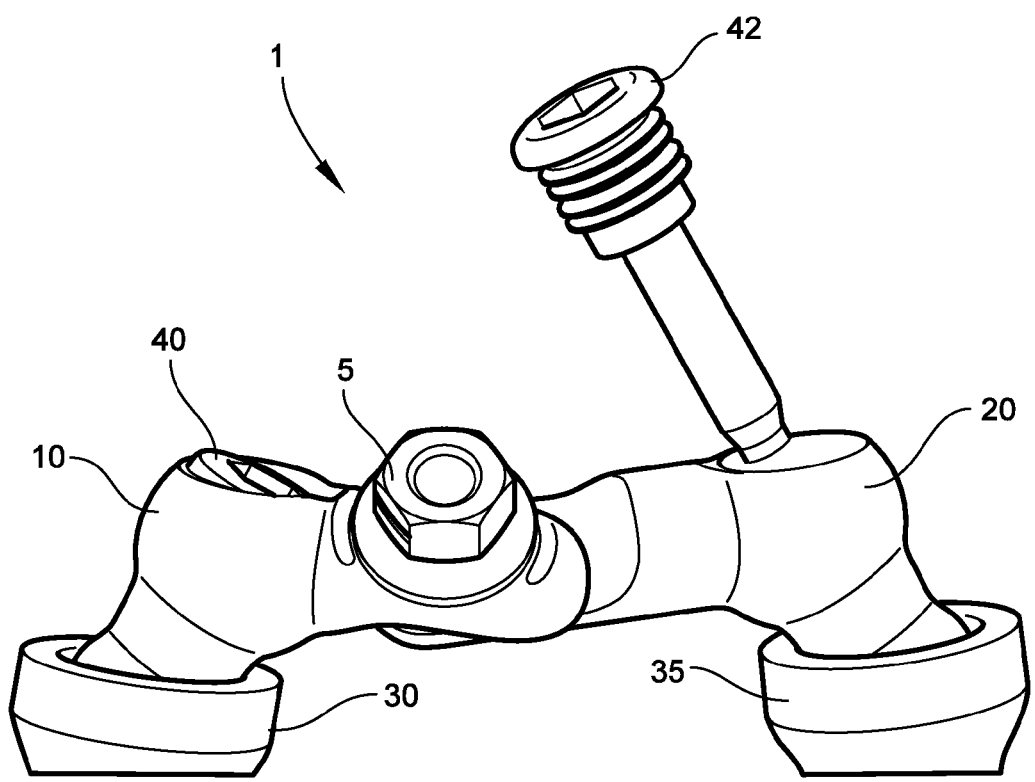
FIG. 1 is a front perspective view of a connection assembly adjoining two polyaxial screw devices, according to an embodiment described herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide an improved headless polyaxial screw device, with fewer components than conventional systems and offering inter-operative flexibility without sacrificing the integrity of the polyaxial screw device, and a method of assembly capable of simplifying a surgical procedure using such an improved headless polyaxial screw device. Referring now to the drawings and more particularly to FIGS. 1 through 23 where similar reference characters denote corresponding features consistently throughout the figures, there are shown preferred embodiments.

FIGS. 1 through 5 provide different perspective views of a polyaxial screw connection system 1 connecting two screw devices, according to an embodiment herein. Connection system 1 comprises fastener 5, first (or top) longitudinal member 10, and second (or bottom) longitudinal member 20. Also shown are two fixation components (e.g., bone screws in one embodiment) 30, 35. Fixation components 30, 35 (as embodied as bone screws) include threaded ends 31, 36, respectively, for engaging a bone (not shown) and a concave female socket end 32, 37, respectively, for engaging and receiving a longitudinal member (e.g., either first longitudinal member 10 or second longitudinal member 20), as further described below.

First longitudinal member 10 and second longitudinal member 20 are illustrated as being snapped into place in fixation components 30, 35, respectively. Then, securing pins 40, 42 are mounted into securing channels 18, 28, respectively, bored into first longitudinal member 10 and second longitudinal member 20, respectively.

Figure 2:
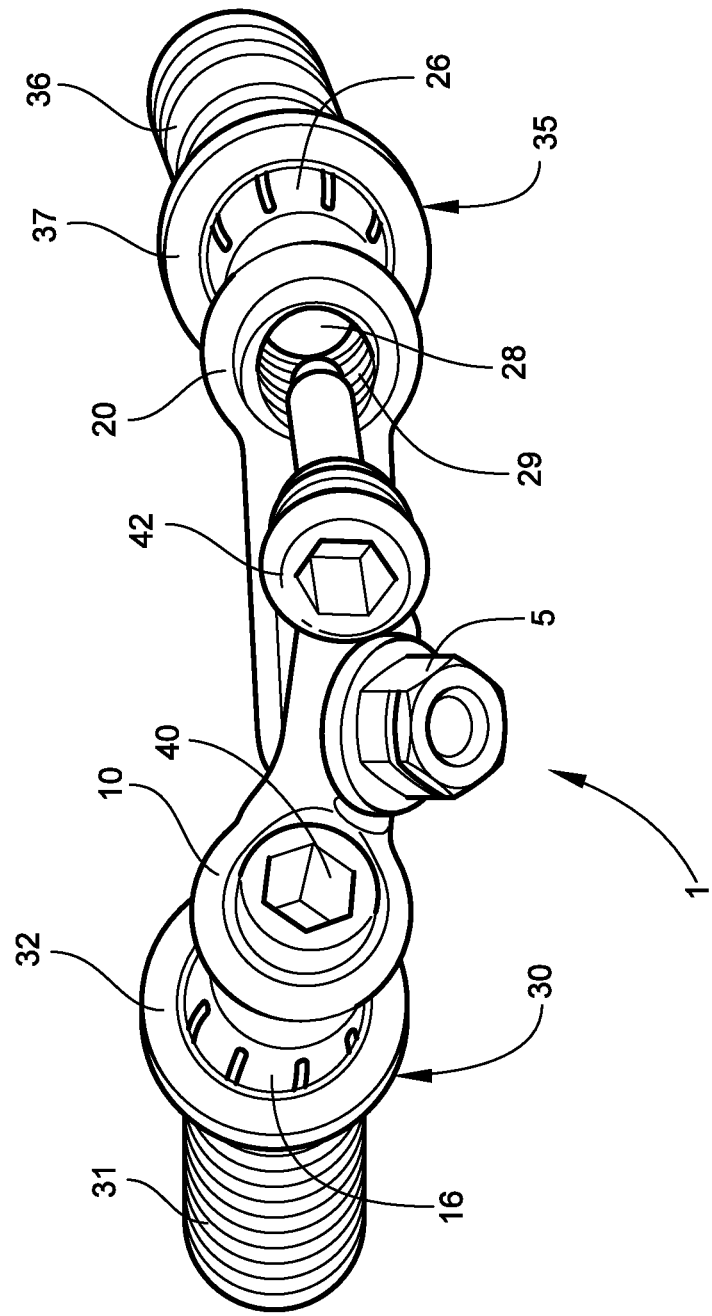
FIG. 2 is a top perspective view of a connection assembly adjoining two polyaxial screw devices, according to an embodiment described herein.
Figure 3:
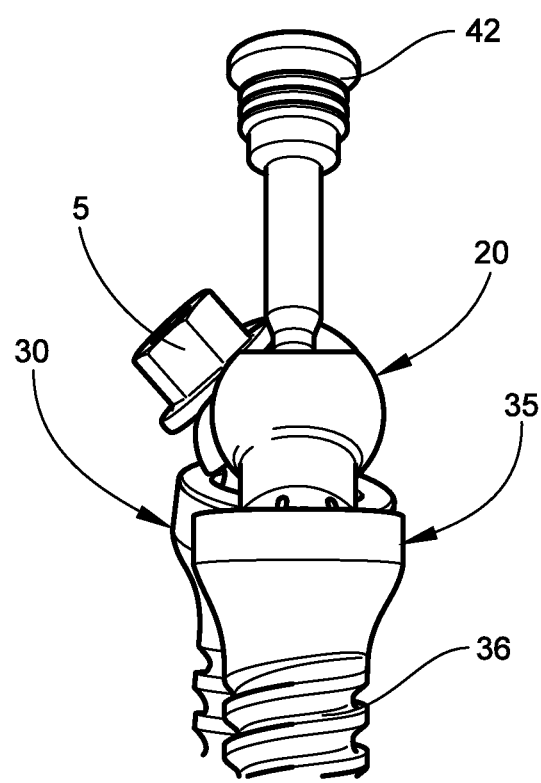
FIG. 3 is a side perspective view of a connection assembly adjoining two polyaxial screw devices, according to an embodiment described herein.
Figure 4:
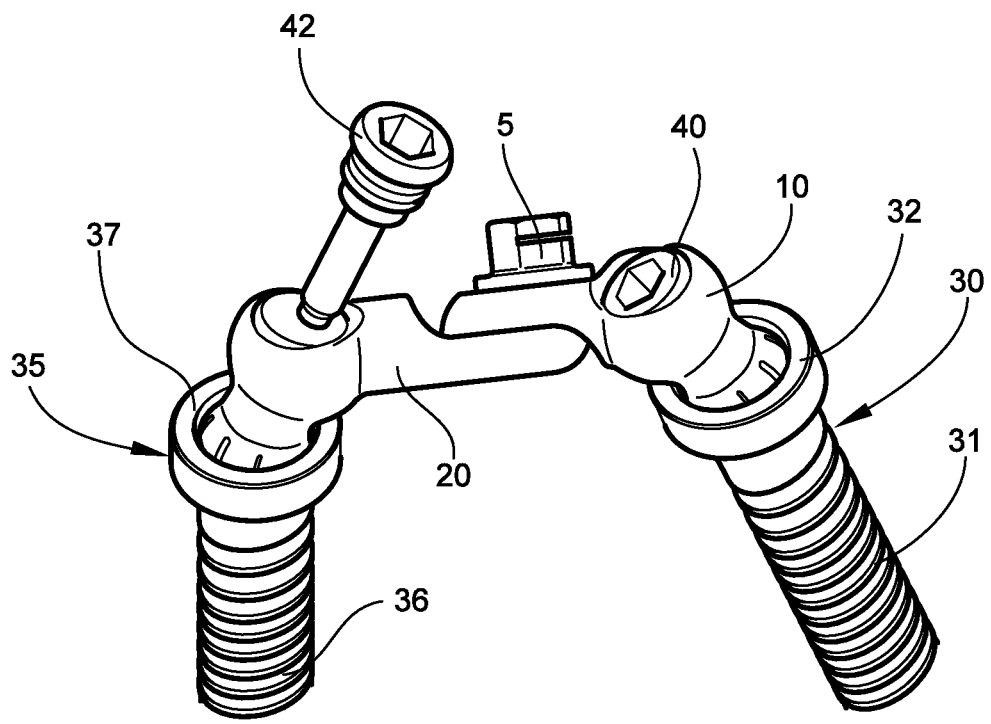
FIG. 4 back perspective view of a connection assembly adjoining two polyaxial screw devices, according to an embodiment described herein.
Figure 5:
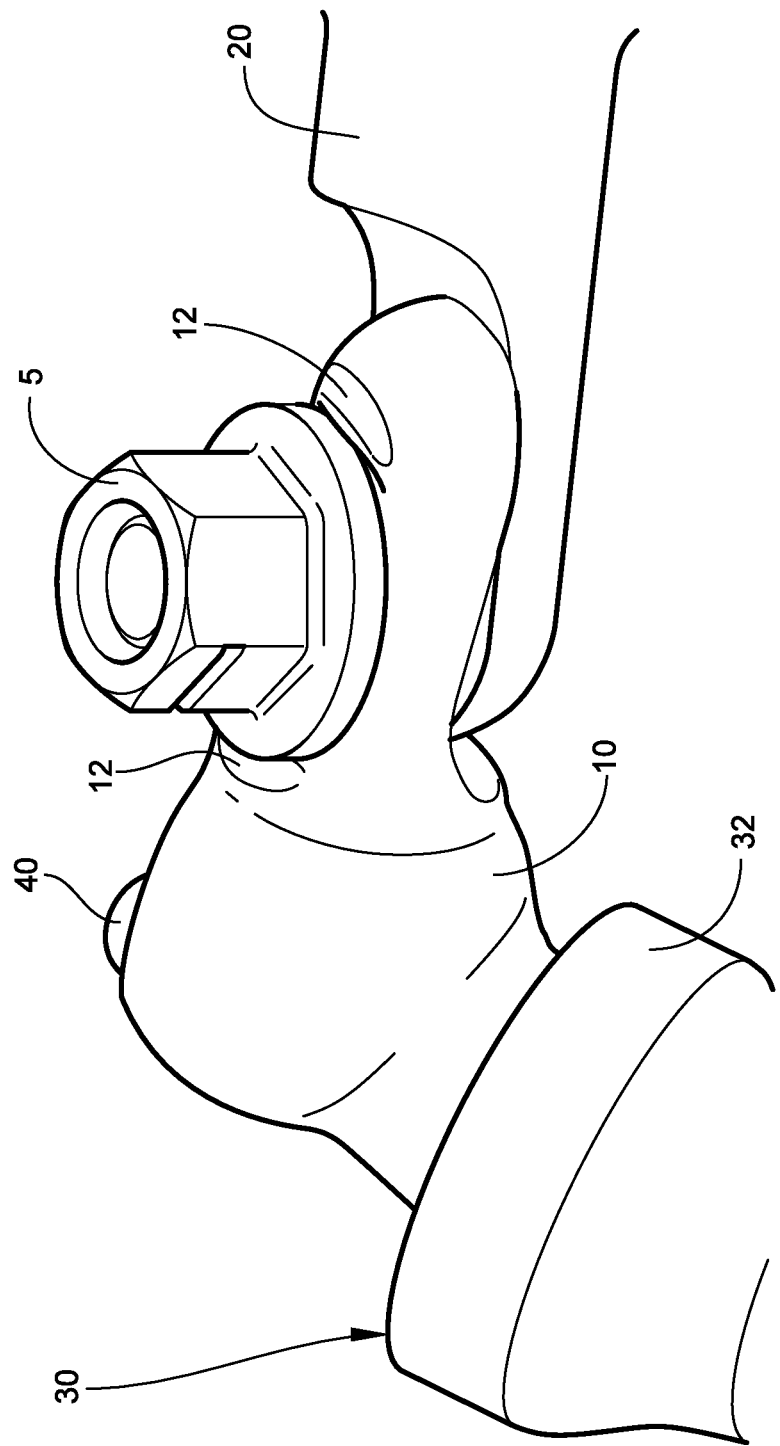
FIG. 5 is a detail view a connection assembly adjoining two polyaxial screw devices, according to an embodiment described herein.

As shown in FIG. 2, securing channel 28 is a substantially vertical bore (i.e., with respect to the longitudinal axis of second longitudinal member 20), and is configured through second longitudinal member 20 and bulbous body 26. While not shown in FIGS. 1 through 5, securing channel 18 is similarly configured. Second longitudinal member 20 comprises threads 29 etched therein, and is configured to mate with threads embedded in securing pin 42 (as described below). While not shown in FIGS. 1 through 5, first longitudinal member 10 is similarly configured.

Figure 6:
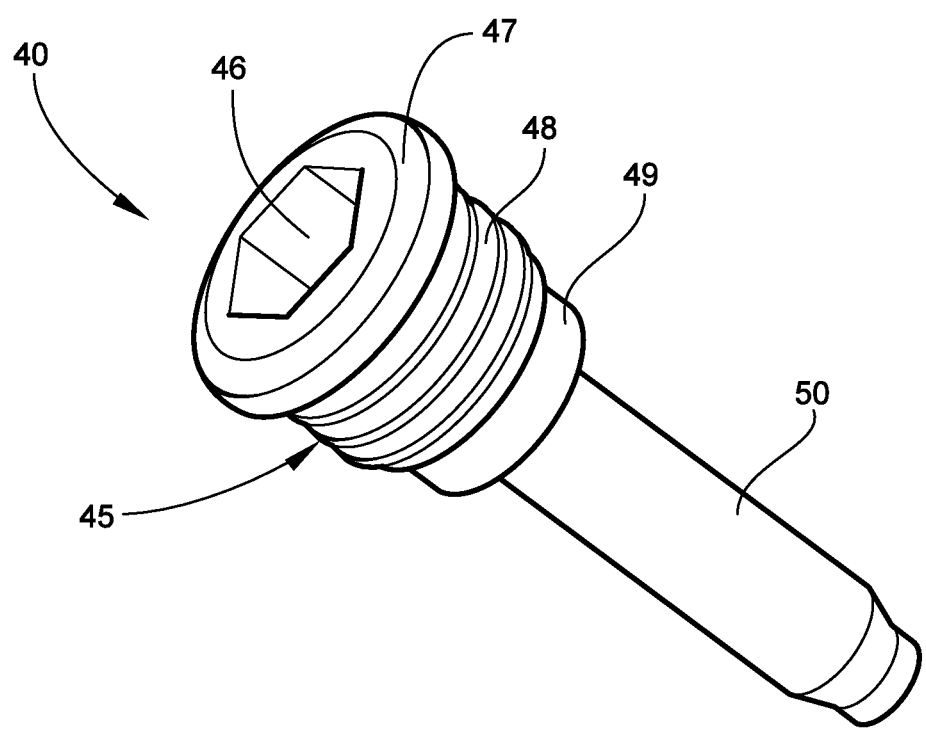
FIG. 6 is a general perspective view of a pin, according to an embodiment described herein.

FIG. 6, with reference to FIGS. 1 through 5, illustrates a side prospective view of securing pin 40. While not shown, securing pin 42 is similarly configured. As shown in FIG. 6, securing pin 40 includes an upper fastening portion 45 and a lower tip portion 50. Upper fastening portion 45 further includes fastening socket 46, pin head 47, threads 48, and connecting ring 49. Although fastening socket 46 is shown a roughly hexagonal, other configurations are possible. For example, fastening socket 46 may be square or any other polygonal shape or may be a linear slit or cross-slit in pin head 47. Threading 48 is embedded around an outer perimeter of upper fastening portion 45 and is configured to engage complimentary threads 29 etched into the inner perimeter of a securing channel 28 shown in FIGS. 1 through 5 bored into a longitudinal member (e.g., second longitudinal member 20). Connecting ring 49 is coupled to both the upper fastening portion 45 and lower tip portion 50. When upper fastening portion 45 and lower tip portion 50 are composed of different materials (as described in further detail below), connecting ring 49 provides additional strength in the coupling thereof.

Securing pin 40 may also comprise a multi-part assembly. For example, the upper fastening portion 45 of securing pin 40 may comprise titanium and the lower tip portion 50 of the securing pin 40 may comprise a ceramic material. Additionally, the lower tip portion 50 may comprise a mechanically harder material than the upper fastening portion 45. In such a configuration, a longitudinal member (e.g., first longitudinal member 10 or second longitudinal member 20) and a fixation component (e.g., fixation components 30 or 35) may optionally comprise a first material, and the lower tip portion 50 of the pin 40 may comprise a material having a higher material hardness and compressive yield strength than the first material. Moreover, connection assembly 1 may further comprise a wear resistant ceramic coating (not shown) over a longitudinal member (e.g., first longitudinal member 10 or second longitudinal member 20) and a fixation component (e.g., fixation components 30 or 35).

Connection assembly 1 can also be used as a dynamic rod system to complement artificial discs. According to this aspect of the embodiments herein, the outside of a bulbous body (e.g., bulbous body 26) and the inner spherical surface of a female socket (e.g., female socket 37) are coated with a wear resistant ceramic coating. In this scenario, the securing pin 40 is not digging into a fixation component (e.g., fixation components 30 or 35) and in fact is configured at a shorter length than some of the other embodiments. This allows some motion between the longitudinal member and fixation component, instead of a rigid fixation, and shares the load with the artificial disc disallowing excessive forces being applied to the artificial disc and increasing its functional life. For example, this occurs as a result of the ceramic coating, which may be used in the embodiments herein. As such, a bulbous body (e.g., bulbous body 26) of a longitudinal member (e.g., second longitudinal member 20) and a female socket (e.g., socket 37) of a fixation component (e.g., fixation component 35) has a lower friction and higher wear resistance characteristics, thus improving the overall movement characteristics of connection assembly 1.

FIGS. 7(A) through 14 illustrate various views of a first, or top, longitudinal member, with reference to FIGS. 1 through 6, according to an embodiment herein. As shown in the various views, first longitudinal member 10 includes fastener channel 11, a plurality of grooves 12, main body 13, lower body 14, top surface 14a, sloping wall 15 connecting the main body 13 and lower body 14, bulbous body 16, a plurality of flanges 17 separated by slits 17a, securing channel 18, and threads 19 etched into an inner perimeter of securing channel 18. FIGS. 7(A) and 7(B) shows longitudinal member 10 including an expandable bulbous (or generally spherical) male body (i.e., bulbous body 16) for engaging concave female socket 32 of fixation component 30. A plurality of axially spaced slots 17a are cut into bulbous body 16 forming a plurality of flanges 17, which expand once securing pin 40 is forced through securing channel 18 and cause the flanges 17 to outwardly project and expand. Also shown in FIG. 7(A) is securing channel 18 as a channel bored through main body 13 and bulbous body 16. As a consequence, the bulbous body 16 expands into female spherical socket 32 of fixation component 30 at any allowable angle and thereby securing longitudinal member 10 to fixation component 30 via bulbous body 16.

Figure 8:
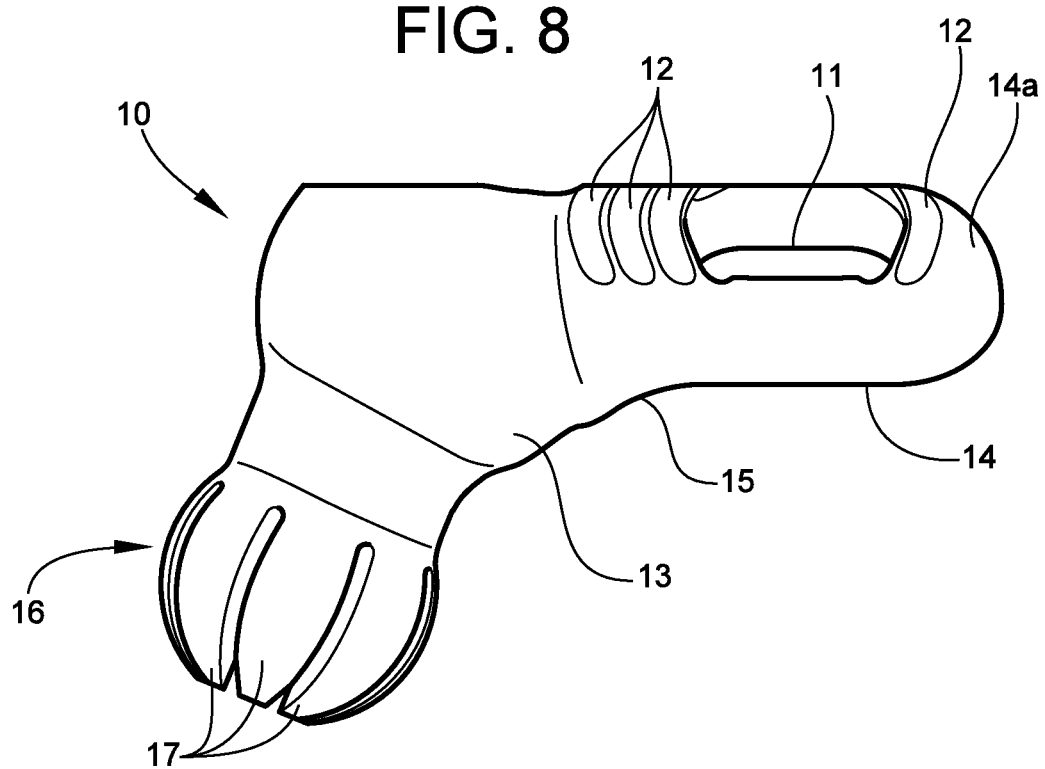
FIG. 8 is a front perspective view of a first longitudinal member, according to an embodiment described herein.

FIG. 8 shows that fastener channel 11 is bored through lower body 14 and may be approximately elliptical in shape (along a horizontal planar cross-section of a longitudinal axis of lower body 14). Although fastener channel 11 is shown in an approximately elliptical configuration, other configurations are possible (including, but not limited to, circular or polygonal configurations) and the embodiments herein are not limited to the shape of fastener channel 11 illustrated in FIGS. 8 through 14.

In addition to fastener channel 11, lower body 14 optionally includes a plurality of grooves 12 etched therein. In the embodiment illustrated in FIGS. 8 through 14, grooves 12 are etched into a top surface 14a of lower body 14, though other configurations are possible and the placement of grooves is not limited to what is shown in the embodiments illustrated. As discussed in further detail below, grooves 12 lock fastener 5 into place and prevent excessive lateral movement of second longitudinal member 20.

Figure 9:
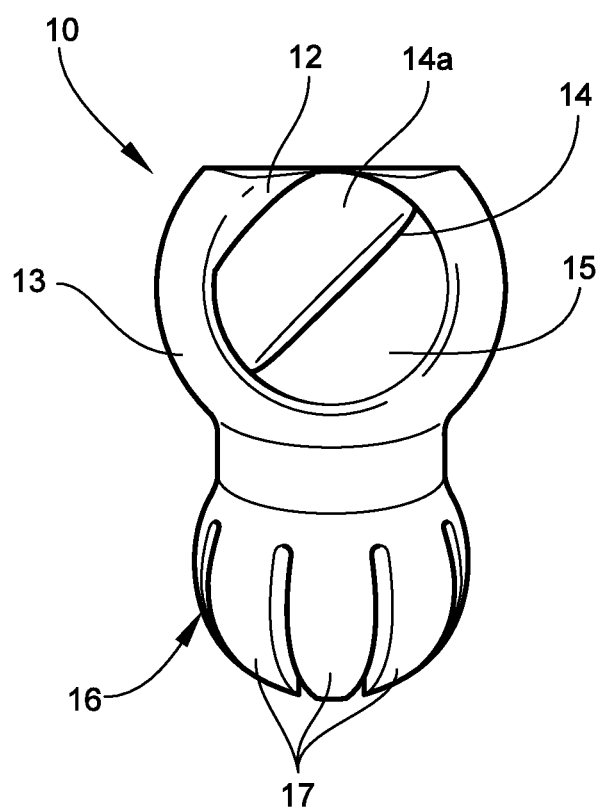
FIG. 9 is a side perspective view of a first longitudinal member, according to an embodiment described herein.
Figure 10:
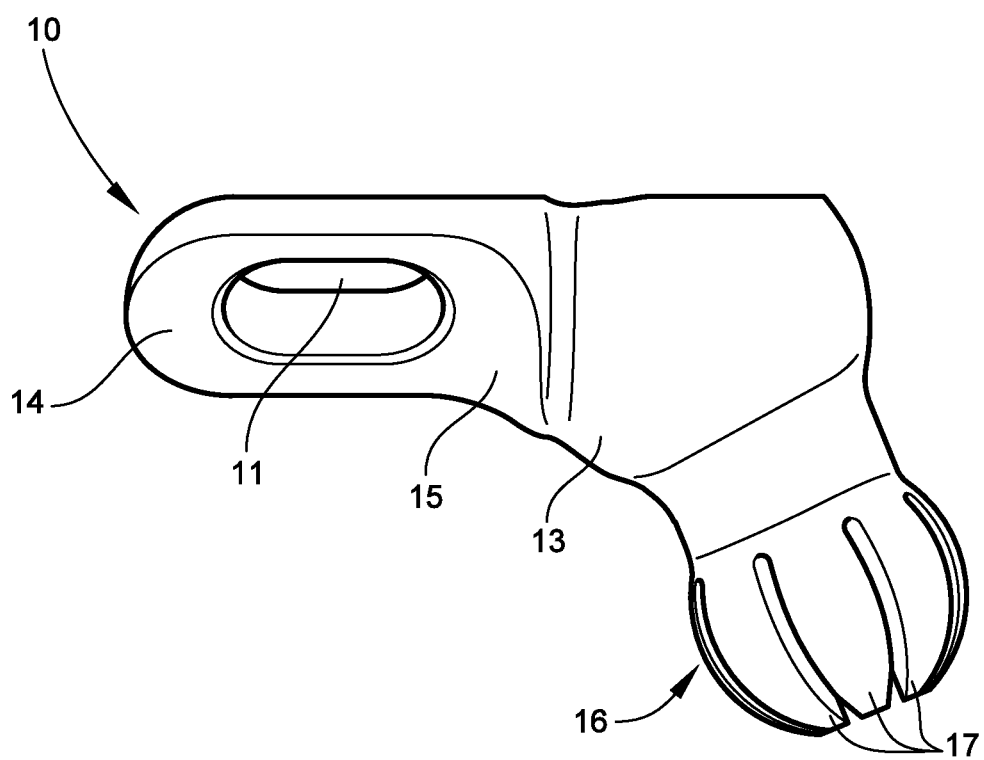
FIG. 10 is a back perspective view of a first longitudinal member, according to an embodiment described herein.

As shown in FIG. 9, lower body 14 is connected to main body 13 via sloping wall 15. Although in the embodiment shown in FIGS. 8 through 14, sloping wall 15 is approximately a 45-degree incline from main body 13 to lower body 14, other angles for sloping wall 15 are possible and the embodiments herein are not limited by the 45-degree incline of sloping wall 15 illustrated. Lower body 14 also has a lateral 45-degree offset from a longitudinal axis spanning between the lower body 14 and main body 13. In other words, the lateral offset of lower body 14 is shown in FIG. 9 as a 45-degree clockwise rotation of lower body 14. While a 45-degree offset from a longitudinal axis spanning between the lower body 14 and main body 13 is shown in FIGS. 7 through 13, other offsets are possible and the embodiments herein are not limited by the 45-degree offset illustrated.

Figure 11:
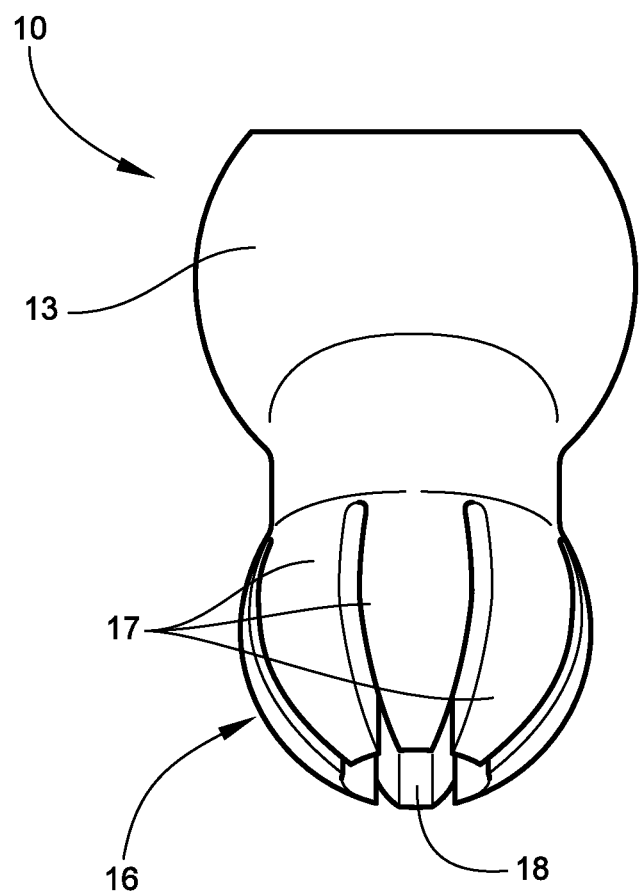
FIG. 11 is another side perspective view of a first longitudinal member, according to an embodiment described herein.
Figure 12:
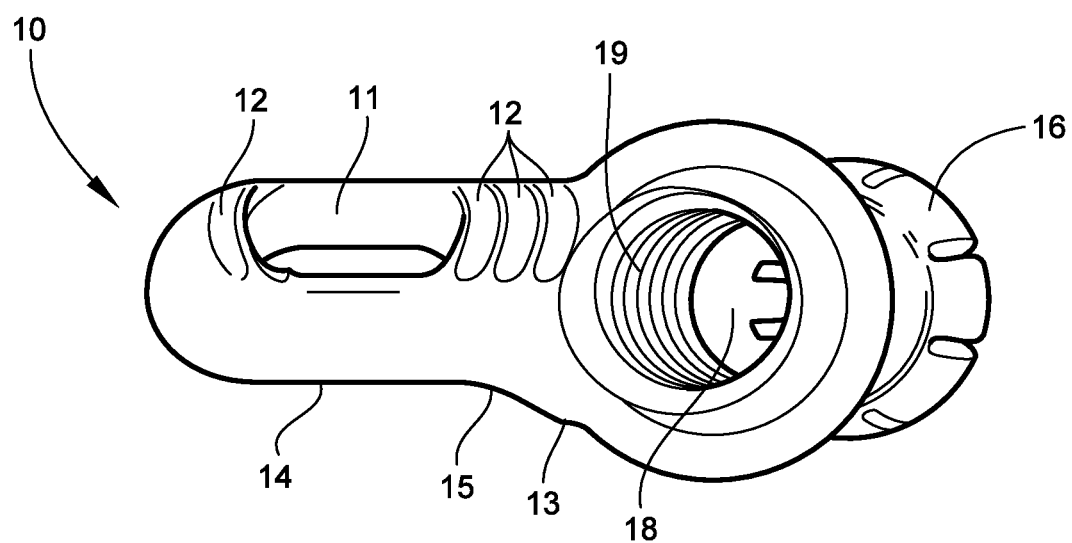
FIG. 12 is a top perspective view of a first longitudinal member, according to an embodiment described herein.
Figure 13:
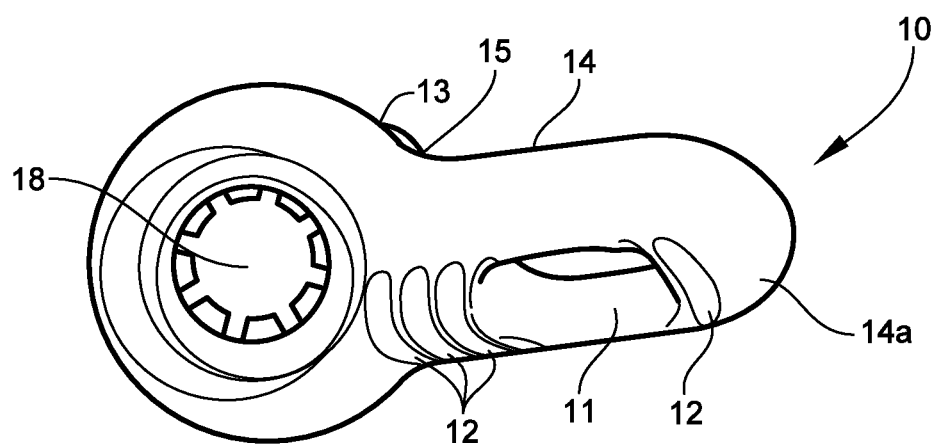
FIG. 13 is another top perspective view of a first longitudinal member, according to an embodiment described herein.
Figure 14:
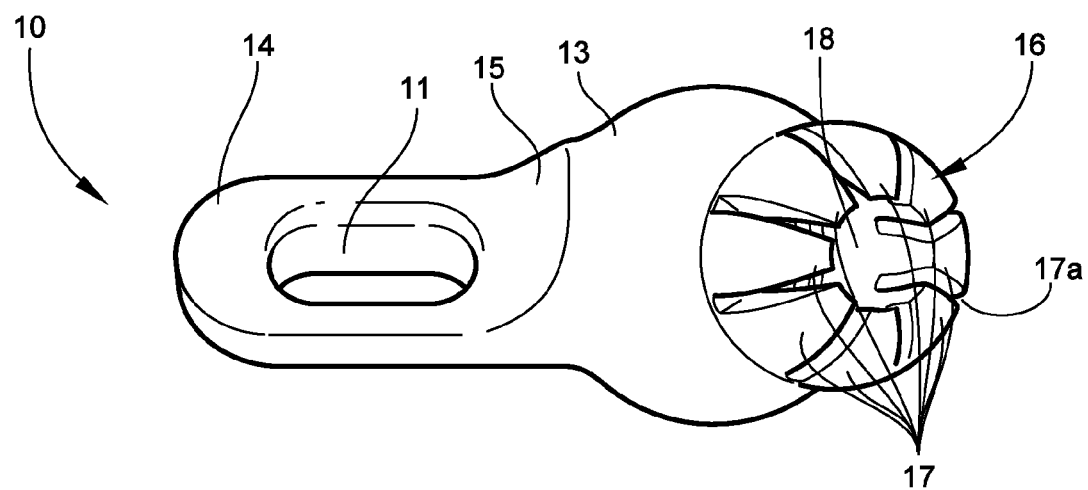
FIG. 14 is a bottom perspective view of a first longitudinal member, according to an embodiment described herein.

Coupled to main body 13 is bulbous body 16, with flanges 17 separated by slits 17a that are cut into bulbous body 16 (as describe above, with reference to FIGS. 7(A) and 7(B)). As shown, securing channel 18 is bored through main body 13 and through bulbous body 16. Alternatively, securing channel 18 may be partially bored through main body 13 and bulbous body 16. Furthermore, securing channel 18 is optionally etched with threads 19 (as shown in FIG. 11) that match and mate with the threads 48 of securing pin 40.

FIGS. 15(A) through 21 illustrate various views of a second, or bottom, longitudinal member 20, with reference to FIGS. 1 through 14, according to an embodiment herein. As shown in the various views, second longitudinal member 20 includes cylindrical body 21, optional threads 22, main body 23, lower body 24, top surface 24a, sloping wall 25 connecting the main body 23 and lower body 24, bulbous body 26, a plurality of flanges 27 separated by slits 27a, securing channel 28, and threads 29 etched into an inner perimeter of securing channel 28. As shown in FIGS. 15(A) and 15(B), longitudinal member 20 includes an expandable bulbous (or generally spherical) male body (i.e., bulbous body 26) for engaging concave female socket 37 of fixation component 35. A plurality of axially spaced slots 27a are cut into bulbous body 26 forming a plurality of flanges 27, which expand once a securing pin 42 is forced through securing channel 28 and cause the flanges 27 to outwardly project and expand. Also shown in FIG. 15(A) is securing channel 18 as a channel bored through main body 13 and bulbous body 13. As a consequence, bulbous body 26 expands into female spherical socket 37 of fixation component 35 at any allowable angle and thereby securing longitudinal member 20 to fixation component 35 via bulbous body 26.

As illustrate in FIG. 16, cylindrical body 21 is fixedly coupled to lower body 24 of second longitudinal member 20. Although cylindrical body 21 is shown as approximately a cylinder, other configurations are possible (including, but not limited to, spherical or cubic configurations) and the embodiments herein are not limited to the shape of cylindrical body 21 illustrated in FIGS. 15(A) through 20.

Figure 17:
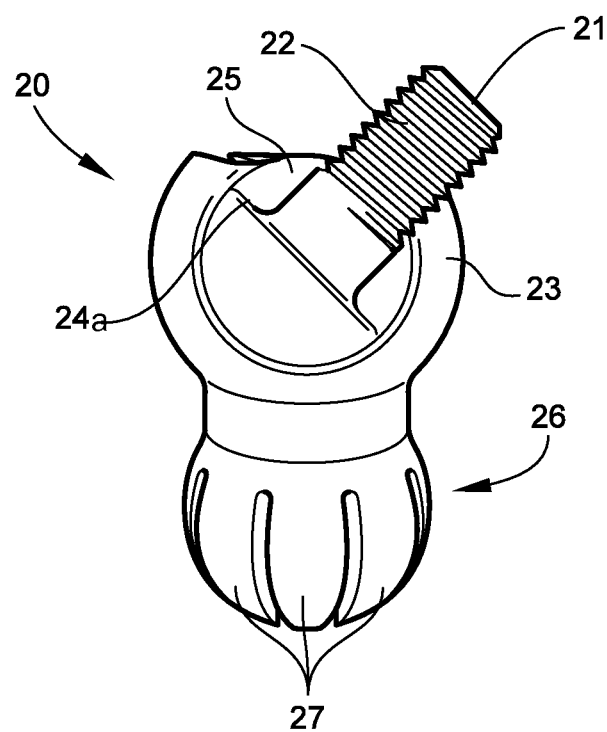
FIG. 17 is a side perspective view of a second longitudinal member, according to an embodiment described herein.
Figure 18:
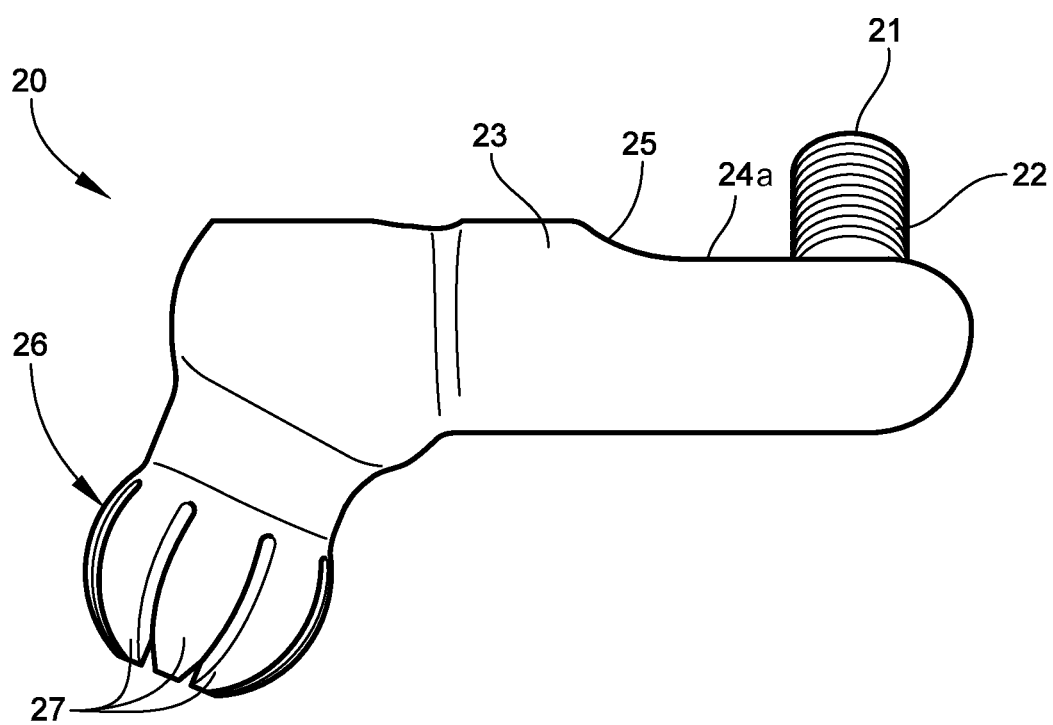
FIG. 18 is a back perspective view of a second longitudinal member, according to an embodiment described herein.
Figure 19:
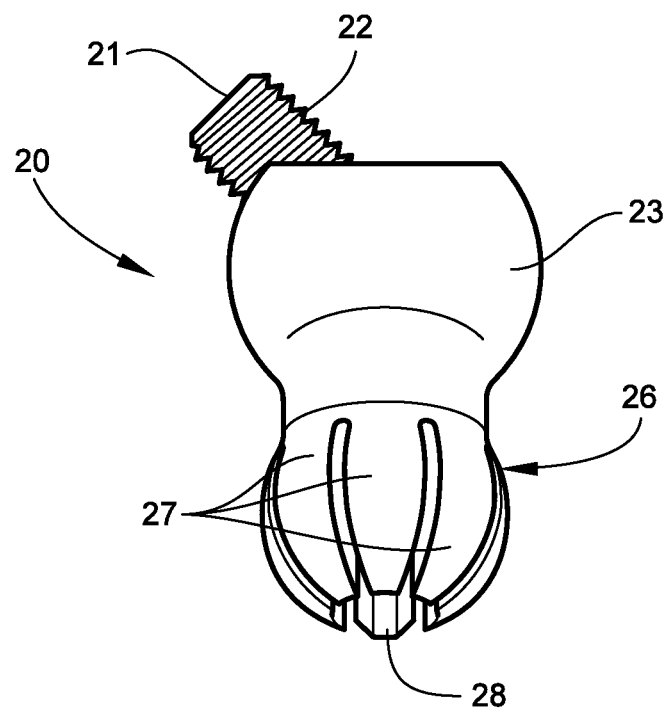
FIG. 19 is another side perspective view of a second longitudinal member, according to an embodiment described herein.

In addition, cylindrical body 21 optionally includes threads 22 embedded therein. As discussed in further detail below, threads 22 are configured to mate with corresponding threads etched into fastener 5. In FIG. 17, lower body 24 is shown as being connected to main body 23 via sloping wall 25. Although in the embodiment shown in FIGS. 15(A) through 20, sloping wall 25 is approximately a 45-degree incline from main body 23 to lower body 24, other angles for the incline for sloping wall 25 are possible and the embodiments herein are not limited by the 45-degree incline of sloping wall 25 illustrated. Lower body 24 also has a lateral 45-degree offset from a longitudinal axis spanning between the lower body 24 and main body 23. In other words, the lateral offset of lower body 24 is shown in FIG. 17 as a 45-degree clockwise rotation of lower body 24. While a 45-degree offset from a longitudinal axis spanning between the lower body 24 and main body 23 is shown in FIGS. 15(A) through 20, other offsets are possible and the embodiments herein are not limited by the 45-degree offset illustrated.

Figure 20:
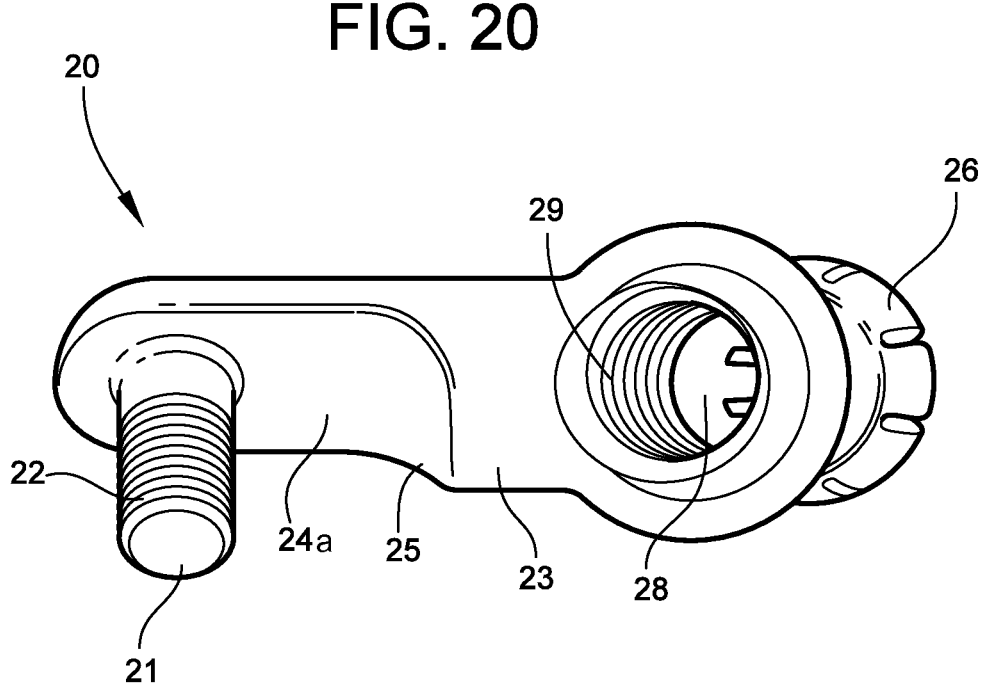
FIG. 20 is a top perspective view of a second longitudinal member, according to an embodiment described herein.
Figure 21:
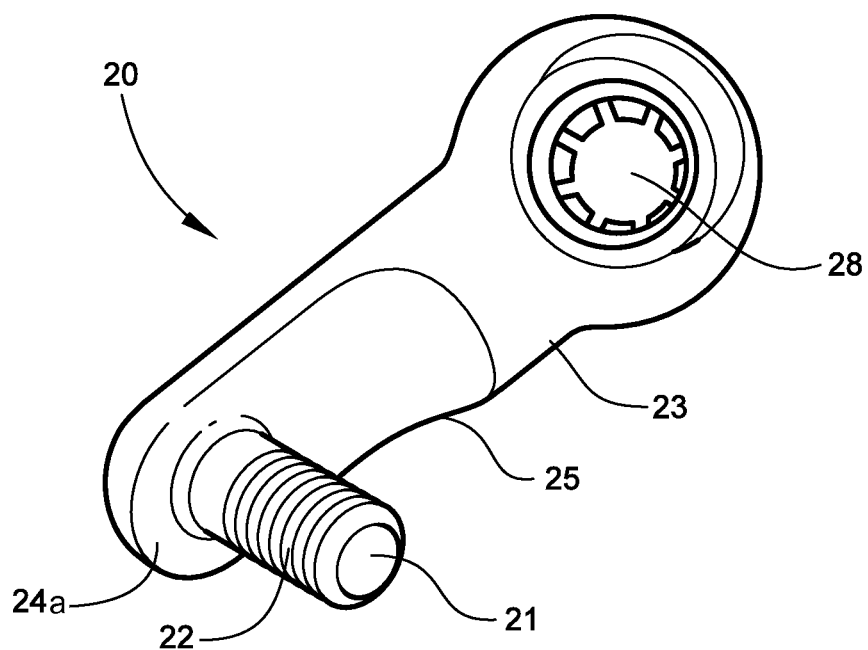
FIG. 21 is another top perspective view of a second longitudinal member, according to an embodiment described herein.

As described above, with reference to FIGS. 15(A) and 15(B), FIG. 19 shows another view of main body 23 coupled to bulbous body 26, with flanges 27 separated by slits 27a cut into bulbous body 26. Securing channel 28 is also shown in FIG. 20 as being bored through main body 23. Alternatively, securing channel 28 may be partially bored through main body 23 and bulbous body 26. Furthermore, securing channel 28 is optionally etched with threads 29 (as shown in FIG. 20) that match and mate with the optional threads of securing pin 42.

Figure 22:
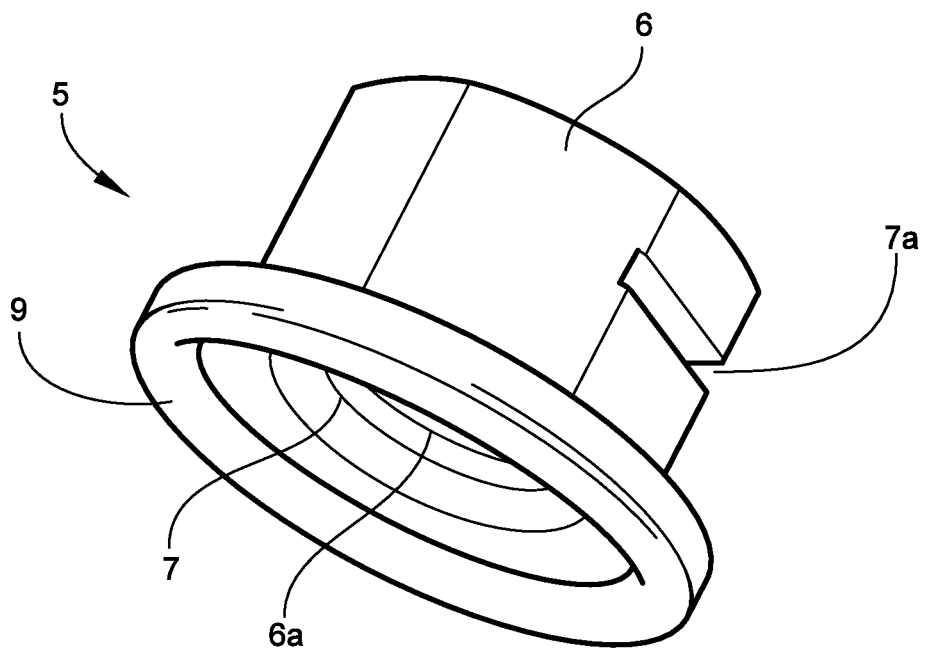
FIG. 22 is a general perspective view of a fastener, according to an embodiment described herein.
Figure 23:
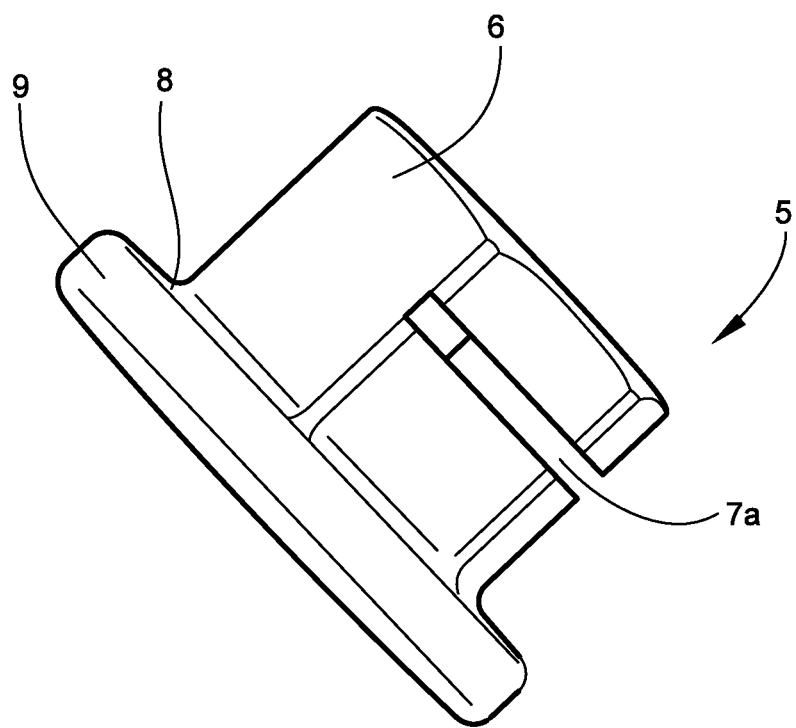
FIG. 23 is another general perspective view of a fastener, according to an embodiment described herein.

FIGS. 22 and 23 illustrated various views of a fastener 5, with reference to FIGS. 1 through 21, according to an embodiment herein. As shown, fastener 5 includes upper portion 6, cylindrical channel 6a bored therethrough, optional threads 7 that are etched in the inner perimeter of upper portion 6, slit 7a, lower portion 8, and ridge 9, which surrounds the outer perimeter of lower portion 7. In FIG. 22, upper portion 6 is shown as having approximately a hexagonal longitudinal cross-section. The hexagonal configuration shown allows a surgeon to use mechanical assistance (such as a wrench or other leveraging device) when securing fastener 5 to cylindrical body 21. Other configurations are possible, however, and include, but are not limited to, a smooth cylindrical configuration or a "wing nut" configuration.

Upper portion 6 has cylindrical channel 6a bored therethrough and is configured to mate with cylindrical body 21. Optionally, the perimeter of cylindrical channel 6a may be etched with threads 7 that are configured to mate with threads 22 etched into the perimeter of cylindrical body. To ensure fastener 5 does not become loose after final engagement with cylindrical body 21 (e.g., by moving along threads 22), slit 7a may be used to lock fastener 5 in place onto cylindrical body 21 and threads 22. As shown, slit 7a is a lateral cut through upper portion 6 to lock threads 22 in place once fastener 5 is securely engaged with cylindrical body 21.

Lower portion 8 is distinctly shaped from upper portion 7 and is securely coupled to upper portion 7. In FIGS. 22 and 23, lower portion 8 is approximately circular in shape, although other configurations are possible. Ridge 9 surrounds the outer perimeter of lower portion 8 and, as seen in FIG. 23, extends below lower portion 8. Ridge 9 is configured to mate with grooves 12 to secure the fastener 5 and cylindrical body 21 combinations in place and prevent any lateral movement thereof. As shown in the embodiments illustrated in FIGS. 8 through 14, grooves 12 may be placed on either side of fastener channel 11 and may be spaced at different distances on either side of fastener channel 11. In the configuration shown in FIG. 8, for example, grooves 12 can accommodate different configurations of fastener 5 and/or different configurations of ridge 9.

FIG. 24, with reference to FIGS. 1 through 23, is a flow diagram illustrating a method of engaging a pedicle fixation assembly 1 to a vertebral body (not shown) according to an embodiment herein. The method of FIG. 24 describes attaching (50) a first bone fixation component 30 to a first vertebra (not shown) of the vertebral body (not shown), wherein the first bone fixation component 30 comprises a first open concave socket 32. Next, the method of FIG. 24 describes attaching (55) a second bone fixation component 35 to a second vertebra (not shown) of the vertebral body (not shown), wherein the second bone fixation component 35 comprises a second open concave socket 37. The next step involves directly attaching (60) a first longitudinal member 10 to the first bone fixation component 30, wherein the first longitudinal member 10 comprises a fastener channel 11 and an outwardly protruding and expandable round first bulbous body 16 that fits into the first concave socket 32. The following step involves directly attaching (65) a second longitudinal member 20 to the second bone fixation component 35, wherein the second longitudinal member 20 comprises an outwardly protruding cylindrical body 21 dimensioned to fit within the fastener channel 11 and an outwardly protruding and expandable round second bulbous body 26 that fits into the second concave socket 37. Thereafter, a first pin 40 is inserted (70) through a first channel 18 bored through the first longitudinal member 10 to contact the first bulbous body 16 causing the first bulbous body 16 to outwardly expand into the first concave socket 32. Subsequently, a second pin 42 is inserted (75) through a second channel 28 bored through the second longitudinal member 20 to contact the second bulbous body 26 causing the second bulbous body 26 to outwardly expand into the second concave socket 37. The method of FIG. 24 further describes inserting (80) the cylindrical body 21 of the second longitudinal member 20 through the fastener channel 11 of the first longitudinal member 10. Thereafter, a fastener 5 is coupled (85) to the cylindrical body 21 to contact the first longitudinal member 10, thereby securing the second longitudinal member 20 to the first longitudinal member 10.

While the steps shown in FIG. 24 are in a specific sequence, the method described therein is not limited to the illustrated sequence. For example, steps 55 and 60 may be performed in reverse order. Moreover, the numerous changes to the method shown in FIG. 24 may be performed by those skilled in the art without requiring undue experimentation (e.g., applying steps 55 and 60 in a reverse order). Changes to the method shown in FIG. 24, which do not require undue experimentation, are embodiments which are not discussed further herein but do constitute embodiments that offer the same benefits and features as the other embodiments described herein.

The method described in FIG. 24 may also be performed by an automatic apparatus, or an otherwise non-human device, or encoded within a computer-readable medium. Automatic devices may include, for example, a robotic arm or remote controlled automata. In general, such devices may assist a human operator or be fully automated (i.e., without the aid of human input). Example of the former include surgical procedures performed via a remote control and devices used in telemedicine, while examples of the latter include a robotic surgeon and nursing robots, which are fully automated but assist a human surgeon.

The embodiments herein provide a headless polyaxial pedicle connection screw assembly 1, or generally a posterolateral connection and fixation system, which may be used anteriorly or posteriorly, and which is capable of being utilized in surgeries to achieve anterior lumbar interbody fusion, posterior lumbar interbody fusion, transverse lumbar interbody fusion, correct degenerative disc disease, adult and pediatric scoliosis as a fixation device, and posterior cervical fusion. The embodiments herein are improvements in the field of orthopedic treatment, such as surgical lumbar and thoracic spine treatment. An adaptation of the embodiments herein may also be utilized in cases where it is not pertinent to perform a spinal fusion; the only requirement being motion limitation in the particular motion segment.

Moreover, the embodiments herein provide a polyaxial spinal screw connection assembly 1 that can become rigid similar to a monoaxial screw inter-operatively on demand. The embodiments herein also offer the surgeon more lateral range of motion than conventional products by utilizing the space between first longitudinal member 10 and second longitudinal member 20 to provide a bigger arc of rotation. The embodiments herein also allows for polyaxial direct connection from first longitudinal member 10 and second longitudinal member 20 to the bone anchor 10. Furthermore, increase the range of motion without sacrificing structural integrity and by reducing the amount of components, to thereby reduce the amount of foreign materials to be implanted during the surgical procedure, the embodiments herein provide a patient with an improved prognosis for better and faster rehabilitation.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:
1. An assembly comprising:
a first longitudinal member comprising a fastener channel bored therethrough and an outwardly protruding and expandable round first bulbous body;
a second longitudinal member comprising an outwardly protruding cylindrical body, dimensioned to fit within said fastener channel, and an outwardly protruding and expandable round second bulbous body;
a fastener with a cylindrical channel bored therethrough, connected to said first longitudinal member and said cylindrical body of said second longitudinal member and securely coupling said first longitudinal member to said second longitudinal member;
a first fixation component directly connected to said first bulbous body wherein said first fixation component receives said first bulbous body;
a second fixation component directly connected to said second bulbous body wherein said second fixation component receives said second bulbous body;
a first pin engaged within said first longitudinal member via a first securing channel bored therethrough and contacting said first bulbous body causing said first bulbous body to outwardly expand; and
a second pin engaged within said second longitudinal member via a second securing channel bored therethrough and contacting said second bulbous body causing said second bulbous body to outwardly expand,
wherein said first longitudinal member includes concentric grooves etched into a top surface of said first longitudinal member,
wherein at least one of said first longitudinal member and said second longitudinal member includes a lower body coupled to a main body by a sloping wall,
wherein said lower body is offset along a longitudinal axis of the main body by 45-degrees, and
wherein said first longitudinal member and said second longitudinal member comprise a single axis of rotation with respect to one another.
2. The assembly of claim 1, wherein said first fixation component comprises a first concave socket that receives said first bulbous body of said first longitudinal member and said second fixation component comprises a second concave socket that receives said second bulbous body of said second longitudinal member.
3. The assembly of claim 1, wherein at least one of said first securing channel and second securing channel comprises threads.

4. The assembly of claim 1, wherein said fastener includes threads etched on an inner perimeter of said cylindrical channel.

5. The assembly of claim 1, wherein said fastener includes a slit along a longitudinal axis thereof.

6. The assembly of claim 1, wherein said fastener is substantially polygonal in shape.

7. The assembly of claim 1, wherein said fastener includes a ridge along an outer perimeter of said fastener and dimensioned to engage said concentric grooves etched into said top surface of said first longitudinal member.

8. An assembly comprising:
   a longitudinal member comprising a fastener channel bored therethrough and an outwardly protruding and expandable round bulbous body, wherein said longitudinal member and said bulbous body comprise a single structure;
   a fixation component directly connected to said bulbous body, wherein said fixation component receives said bulbous body; and
   a pin engaged within said longitudinal member via a securing channel bored through said longitudinal member and contacting said bulbous body causing said bulbous body to outwardly expand,
   wherein said longitudinal member includes concentric grooves etched into a top surface of said longitudinal member,
   wherein said longitudinal member includes a lower body coupled to a main body by a sloping wall, and
   wherein said lower body is offset along a longitudinal axis of the main body by 45-degrees.

9. The assembly of claim 8, wherein said fastener channel is bored through said lower body.

10. The assembly of claim 8, wherein a shape of said fastener channel is elliptical.

11. An assembly comprising:
    a pair of longitudinal members each comprising a fastener channel bored therethrough and an outwardly protruding and expandable round bulbous body;
    a pair of fixation components, wherein each fixation component is directly connected to one of said bulbous bodies, wherein each said fixation component receives a corresponding bulbous body;
    a pair of pins, wherein each pin is engaged within a corresponding longitudinal member via a securing channel and contacts a corresponding bulbous body causing said bulbous body to outwardly expand; and
    exactly one fastener comprising a cylindrical channel bored therethrough, connecting said pair of longitudinal members to each other,
    wherein at least one of said pair of longitudinal members includes concentric grooves etched into a top surface of said longitudinal member,
    wherein said at least one of said pair of longitudinal members includes a lower body coupled to a main body by a sloping wall,
    wherein said lower body is offset along a longitudinal axis of the main body by 45-degrees, and
    wherein said pair of longitudinal members comprise a single axis of rotation with respect to one another.

12. The assembly of claim 11, wherein said plurality of concentric grooves are spaced apart from one another.

* * * * *